United States Patent
Rodefeld

(10) Patent No.: US 6,759,558 B2
(45) Date of Patent: Jul. 6, 2004

(54) PROCESS FOR PREPARING HALOGEN-SUBSTITUTED DIBENZYL ALCOHOLS, THESE HALOGEN-SUBSTITUTED DIBENZYL ALCOHOLS AND THEIR USE

(75) Inventor: Lars Rodefeld, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/117,523

(22) Filed: Apr. 5, 2002

(65) Prior Publication Data

US 2002/0156330 A1 Oct. 24, 2002

(30) Foreign Application Priority Data

Apr. 6, 2001 (DE) .......................... 101 17 206

(51) Int. Cl.$^7$ .............................................. C07C 33/28
(52) U.S. Cl. ....................................................... 568/811
(58) Field of Search ........................................ 568/811

(56) References Cited

U.S. PATENT DOCUMENTS

| | | | |
|---|---|---|---|
| 2,631,168 A | * | 3/1953 | Ross |
| 3,029,290 A | * | 4/1962 | Lindemann |
| 3,899,466 A | * | 8/1975 | Dubeck |
| 4,107,104 A | * | 8/1978 | Dubeck |
| 4,140,843 A | * | 2/1979 | Widmer |
| 4,141,912 A | * | 2/1979 | Mark |
| 4,301,088 A | * | 11/1981 | Bernhardt |
| 4,590,308 A | * | 5/1986 | Costello |
| 4,927,852 A | | 5/1990 | Robson et al. ............... 514/531 |
| 5,583,131 A | * | 12/1996 | Bridger |
| 6,034,128 A | | 3/2000 | Ujihara ........................ 513/531 |

FOREIGN PATENT DOCUMENTS

| | | |
|---|---|---|
| DE | 37 14 602 | 11/1988 |
| DE | 100 03 320 | 8/2001 |
| EP | 0 959 065 | 11/1999 |
| EP | 0 926 129 | 3/2002 |
| GB | 2127013 | 4/1984 |
| WO | 00/68173 | 11/2000 |

* cited by examiner

Primary Examiner—Michael L. Shippen
(74) Attorney, Agent, or Firm—Godfried R. Akorli; Diderico van Eyl; Jill Denesvich

(57) ABSTRACT

A novel process allows a simple preparation of highly pure halogen-substituted dibenzyl alcohols by reduction of the corresponding halogen-substituted terephthalic acids and reaction with an alkylating agent, sulfuric acid, alkyl- or arylsulfonic acids. The highly pure halogen-substituted dibenzyl alcohols obtained are suitable in particular for preparing pharmaceutically or agrochemically active compounds.

13 Claims, No Drawings

PROCESS FOR PREPARING HALOGEN-SUBSTITUTED DIBENZYL ALCOHOLS, THESE HALOGEN-SUBSTITUTED DIBENZYL ALCOHOLS AND THEIR USE

BACKGROUND

The present invention relates to a process for preparing halogen-substituted dibenzyl alcohols from the corresponding halogen-substituted terephthalic acids, to the halogen-substituted dibenzyl alcohols obtainable by this process and to their use for preparing pharmaceutically and agrochemically active compounds.

2,3,5,6-Tetrahalodibenzyl alcohols are known to the person skilled in the art as important intermediates, for example for preparing pharmaceutically or agrochemically active compounds such as insecticides. 2,3,5,6-Tetrafluorodibenzyl alcohol, in particular, is an important intermediate in the preparation of insecticidally active pyrethroids.

The use of 2,3,5,6-tetrafluorodibenzyl alcohol as a starting material in the preparation of household insecticides is described, for example, in EP-A-0 963 976, EP-A-0 959 065, EP-A-0 302 612 and EP-A-0 926 129.

The preparation of 2,3,5,6-tetrafluorodibenzyl alcohol by borohydride reduction from derivatives of tetrafluoroterephthalic acid is described in GB-A-2,127,013. Here, the reduction of tetrafluoroterephthalic acid chloride is carried out using sodium borohydride in diglyme at a temperature of 20° C. giving the tetrafluorodibenzyl alcohol in a yield of only 64.4%. Nothing is said about the purity.

Furthermore, WO-A-00/68173 describes the synthesis of tetrafluorodibenzyl alcohols by catalytic reduction of the corresponding tetrafluoroterephthalonitrile via the intermediates tetrafluoroterephthalaldehyde tetraalkyl acetal and tetrafluoroterephthalaldehyde. However, in the case of the preparation of 2,3,5,6-tetrafluorodibenzyl alcohol, a purity of only 93.4% is obtained. The total yield, starting from 2,3,5,6-tetrafluoroterephthalonitrile, is 48% (see Examples 15 and 18 in this document). Also described is the synthesis of 2,3,5,6-tetrafluorobenzyl alcohol by the same process. The yields of about 80% and the purities of >99% described in a number of examples in this document are considerably higher than those in the synthesis of the corresponding dibenzyl alcohol.

The synthesis of 2,3,5,6-tetrafluorodibenzyl alcohol is also described in the as yet unpublished German patent application with the reference 100 03 320, by hydrogenation of 2,3,5,6-tetrafluoroterephthalonitrile to 2,3,5,6-tetrafluorodibenzylamine and subsequent diazotization and heating of the amine. The 2,3,5,6-tetrafluorodibenzyl alcohol obtained in this manner has a purity of 74.5%; however, for certain applications, this is still not entirely satisfactory. According to the example, the total yield starting from 2,3,5,6-tetrafluoroterephthalonitrile is 52.1%.

WO-A-00/68173 describes a process in which, comparably to the process of the German patent application with the reference 100 03 320, 2,3,5,6-tetrafluorobenzyl alcohol is prepared from 2,3,5,6-tetrafluorobenzonitrile. The purity of 99.3% and the yield of 85.1% achieved here are considerably higher than those achieved in the synthesis of the corresponding 2,3,5,6-tetrafluorodibenzyl alcohol.

DE-A-37 14 602 describes a process for preparing 2,3,5,6-tetrafluorobenzyl alcohols which may be substituted in the 4-position by a methyl radical, by reacting 2,3,5,6-tetrafluorobenzoic acids which may be substituted in the 4-position by a methyl radical with sodium borohydride and then with an alkylating agent in the presence of a diluent at temperatures between −20° C. and +150° C. The reaction of the tetrafluorobenzoic acids is preferably carried out at 0–30° C. and the subsequent reaction with the alkylating agent is preferably carried out at 0–100° C., where from 0.5 to 0.9 mol of an alkylating agent are employed per mole of starting material. The process affords the 2,3,5,6-tetrafluorobenzyl alcohol in a yield of 96.7% and a purity of 98%.

The hydrolysis with sulfuric acid of 2,3,5,6-tetrafluoroterephthalonitrile to 2,3,5,6-tetrafluoroterephthalic acid is described in EP-A-0 749 409.

As is known to the person skilled in the art, the use of insecticides, in particular household insecticides, is preceded by intensive toxicological studies. As a consequence, it is desirable to be able to employ the active compounds in a defined form which is as pure as possible. In the synthesis of insecticides—in particular when 2,3,5,6-tetrafluorodibenzyl alcohol is used—the byproducts which are substituted asymmetrically in the benzyl position, such as 1-(benzyl alcohol)-4-benzylamines, 1-benzaldehyde-4-benzyl alcohols and 1-(benzoic acid)-4-benzyl alcohols are disruptive, since these compounds can pass through the entire synthesis and even into the end product, and may therefore remain in the active compound and can exert undesirable toxic effects.

All of the three processes for preparing 2,3,5,6-tetrafluorodibenzyl alcohols mentioned above (GB-A-2,127,013, WO-A-00/68173 and DE-A-100 03 320) have in common the disadvantage that, starting from tetrafluoroterephthalonitrile, the reaction proceeds via more than one intermediate. An additional, decisive disadvantage is the fact that in all other processes used both for preparing monobenzyl alcohols and dibenzyl alcohols, the dibenzyl compound is in each case obtained in a considerably poorer yield and purity. The conclusion that had to be drawn from these facts was that apparently the dibenzyl function of the desired product and the asymmetric intermediates formed during a synthesis greatly affect both purity and yield.

Accordingly, it was an object of the present invention to provide a process which allows the preparation of halogen-substituted dibenzyl alcohols starting from the corresponding halogen-substituted terephthalic acids, with high yields and purities and in particular substantially free of compounds substituted asymmetrically in the 1- and 4-positions.

SUMMARY

The invention relates to a process for preparing a halogen-substituted dibenzyl alcohol of the general formula (I):

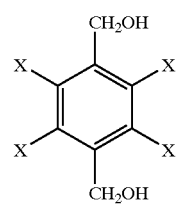

(I)

wherein the radicals X are identical or different and are hydrogen, fluorine, chlorine or bromine and at least one X is fluorine, chlorine or bromine. The process comprises reacting (1) a halogen-substituted terephthalic acid of the general formula (II)

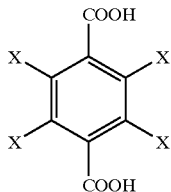
(II)

wherein the radicals X are as defined for the general formula (I) with (2) sodium borohydride and then with (3) an alkylating agent or sulfuric acid or an alkyl-sulfonic acid or an arylsulfonic acid, wherein the sulfuric acid or the alkyl-sulfonic acid or the arylsulfonic acid comprises at most 5% by volume of water and the sodium borohydride reacts in an organic solvent at a temperature ranging from about 0 to about 150° C.

The invention also relates to a halogen-substituted dibenzyl alcohol of the general formula (I):

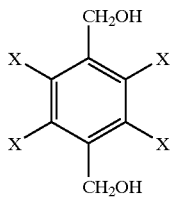
(I)

wherein the radicals X are identical or different and are hydrogen, fluorine, chlorine or bromine and at least one X is fluorine, chlorine or bromine, wherein the alcohol is obtained by a process comprising reacting (1) a halogen-substituted terephthalic acid of the general formula (II)

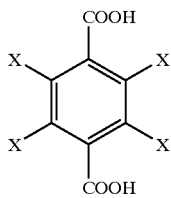
(II)

wherein the radicals X are as defined for the general formula (I) with (2) sodium borohydride and then with (3) an alkylating agent or sulfuric acid or an alkylsulfonic acid or an arylsulfonic acid, wherein the sulfuric acid or the alkylsulfonic acid or the arylsulfonic acid comprise at most 5% by volume of water and the sodium borohydride reacts in an organic solvent at a temperature ranging from 0 to about 150° C.

The invention also relates to a halogen-substituted dibenzyl alcohol of the general formula (I)

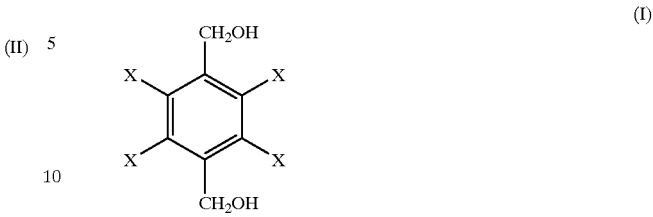
(I)

wherein the radicals X are identical or different and are hydrogen, fluorine, chlorine or bromine and at least one X is fluorine, chlorine or bromine, wherein the alcohol comprises at most 1.0% of compounds which are substituted asymmetrically in the 1- and 4-positions. These and other features, aspects, and advantages of the present invention will become better understood with reference to the following description and appended claims.

DESCRIPTION

The invention provides a process for preparing halogen-substituted dibenzyl alcohols of the general formula (I)

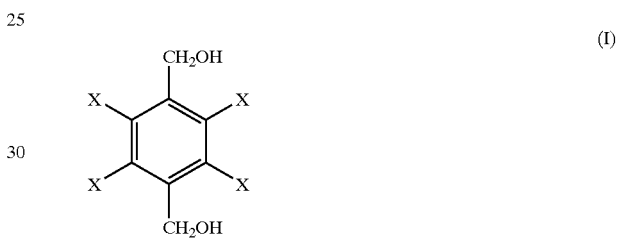
(I)

where the radicals X are identical or different and are hydrogen, fluorine, chlorine or bromine and at least one X is fluorine, chlorine or bromine, by reacting (1) halogen-substituted terephthalic acids of the general formula (II)

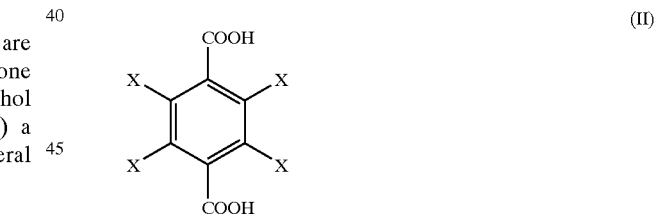
(II)

where the radicals X are as defined for the general formula (I), with (2) sodium borohydride and then with an alkylating agent or sulfuric acid or alkyl- or arylsulfonic acids, where the sulfuric acid or the alkyl- or arylsulfonic acids comprise at most about 5% by volume of water and the reaction with sodium borohydride is carried out in an organic solvent at a temperature in the range of from about 0 to about 150° C.

The borohydride reduction according to the invention of the halogen-substituted terephthalic acids of the general formula (II) under the conditions mentioned and the subsequent reaction with alkylating agent, sulfuric acid or alkyl- or arylsulfonic acid succeeds with an unexpectedly high purity and simultaneously high yield. Products of the formula (I) obtained are substantially free or, in the preferred case, completely free of compounds which are substituted asymmetrically in the 1- and 4-positions, in particular of halogen-substituted 1-(benzyl alcohol)-4-benzylamines, halogen-substituted 1-benzaldehyde-4-benzyl alcohols and halogen-substituted 1-(benzoic acid)-4-benzyl alcohols.

Starting materials for the process according to the invention are halogen-substituted terephthalic acids of the general formula (II) where the radicals X are identical or different and are hydrogen, fluorine, chlorine or bromine and at least one X is fluorine, chlorine or bromine. Preference is given to using 2,3,5,6-tetrafluoro- and 2,3,5,6-tetrachloroterephthalic acid, i.e. all four substituents X are fluorine or chlorine. The use of terephthalic acids having mixed substituents, where two X are hydrogen and in each case one X is chlorine or fluorine has also been found to be useful.

The person skilled in the art is familiar with the preparation of such halogen-substituted terephthalic acids of the general formula (I). The halogenated terephthalic acids of the general formula (II) are preferably prepared by acid hydrolysis of halogenated terephthalonitrile of the general formula (III)

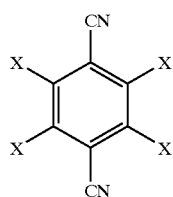

(III)

where the radicals X are as defined for the general formula (III).

This acid hydrolysis can be carried out in a simple manner and with high purities. If this group is chosen for preparing the halogen-substituted terephthalic acid, the halogenated dibenzyl alcohol which is finally obtained by the process according to the invention is particularly pure. This variant has been found to be particularly useful for preparing 2,3,5,6-tetrafluoroterephthalic acid from 2,3,5,6-tetrafluoroterephthalonitrile. In the process according to the invention, the reaction with sodium borohydride is carried out at a temperature in the range of from about 0 to about 150° C., preferably from about 20 to about 80° C. and in particular from about 40 to about 65° C.

The reaction according to the invention with sodium borohydride is carried out in an organic solvent. Preference is given to using an aprotic polar organic solvent, such as, for example, diethyl ether, diisopropyl ether, diisobutyl ether, methyl t-butyl ether, 1,2-dimethoxyethane, diglycol dimethyl ether, tetrahydrofuran and 1,4-dioxane. Particular preference is given to 1,2-dimethoxyethane. In a particular embodiment, sodium borohydride is initially charged and 2,3,5,6-tetrafluoroterephthalic acid is added as a solution in this solvent.

In cases where an alkylating agent is added after the borohydride reduction, it has been found to be useful to employ from about 2.0 to about 2.5 mol, preferably from about 2.1 to about 2.4 mol, particularly preferably from about 2.1 to about 2.3 mol of sodium borohydride per mole of halogenated terephthalic acid of the general formula (II) for the reduction.

In contrast, in cases where sulfuric acid or an alkyl- or arylsulfonic acid is employed after the borohydride reduction, it has been found to be useful to employ from about 2.0 to about 4.0 mol and preferably from about 2.5 to about 3.0 mol of sodium borohydride per mole of halogenated terephthalic acid of the general formula (II) for the reduction.

Suitable for use as alkylating agents are, for example, alkyl halides, dialkyl sulfates and sulfonic esters of the general formulae (IV), (V) and (VI):

R—Hal    RO—SO$_2$—OR$^2$    R—SO$_2$—OR$^2$   $(IV)$ $(V)$ $(VI)$ where R and R$^2$ independently of one another are methyl, ethyl, propyl, isopropyl, n-butyl, isobutyl, tert-butyl, phenyl or tolyl and Hal is Cl, Br or I.

Here, from about 1.0 to about 2.0 mol and preferably from about 1.4 to about 2.0 mol of the alkylating agent are employed per mole of the halogenated terephthalic acid of the general formula (II) originally employed.

In the process according to the invention, it is furthermore also possible to employ, instead of an alkylating agent, sulfuric acid or an alkyl- or arylsulfonic acid which comprises at most about 5% by volume of water. Suitable for use as alkylsulfonic acid are, for example, methyl-, ethyl-, propyl- or butylsulfonic acid. Phenyl- or tolylsulfonic acid have been found to be suitable arylsulfonic acids. In this case, from about 0.5 to about 1.0 mol of sulfuric acid or from about 1.0 to about 2.0 mol of an alkyl- or arylsulfonic acid are usually employed per mole of the halogenated terephthalic acid of the general formula (II) originally employed, where the sulfuric acid or alkyl- or arylsulfonic acid comprises in each case at most 5% by volume of water.

The alkylating agent, too, can be added diluted with an inert solvent. For this purpose, it is possible to use the polar aprotic organic solvents which can be employed for the borohydride reduction. Other inert solvents suitable for diluting the alkylating agent are $C_5$–$C_{30}$-, preferably $C_6$–$C_{12}$-alkanes, $C_5$–$C_{30}$-, preferably $C_6$–$C_{12}$-cycloalkanes, $C_6$–$C_{20}$-, preferably $C_6$–$C_{12}$-aromatics, $C_2$–$C_{10}$-esters and $C_2$–$C_{30}$-ethers. Preference is given to using hexane, heptane, petroleum ether, cyclohexane, decalin, benzene, toluene, the xylenes, chlorobenzene, dichlorobenzene, trichlorobenzene, ethyl acetate, butyl acetate, diethyl ether, tetrahydrofuran and diphenyl ether. Particular preference is given to toluene and xylene.

In the process according to the invention, the reaction with the alkylating agent, the sulfuric acid or the alkyl- or arylsulfonic acid is carried out, for example, at temperatures in the range from about 0 to about 150° C., preferably from about 30 to about 80° C., particularly preferably from about 40 to about 70° C. and especially from about 50 to about 65° C.

The process according to the invention is usually carried out at atmospheric pressure or at an elevated pressure of up to about 10 bar.

Work-up and isolation of the reaction product can be carried out by customary methods. Preferably, the reaction mixture is diluted with a solvent which is virtually water-immiscible. Also advantageous is the option of solvent exchange by distillation. Particularly advantageous is the use of the diluent of the alkylating agent for this purpose. It is then possible to hydrolyze using water or an aqueous acid. The aqueous phase can be extracted, if appropriate at elevated temperature, and the product can then be crystallized from the extraction agent, for example after concentration or again after solvent exchange, to reduce the solubility of the product in the solvent, and be isolated by filtration.

In the work-up steps, such as, for example, the distillation, it has been found to be useful to lower the pressure to about 0.001 bar.

By the simple process steps of a borohydride reduction and reaction with alkylating agent, sulfuric acid, alkyl- or arylsulfonic acid, the process according to the invention affords the desired halogenated dibenzyl alcohol of the general formula (I) in a purity of more than about 98.5%, with at the same time excellent high yields.

Accordingly, the invention furthermore provides the halogen-substituted dibenzyl alcohols of the general formula (I) which can be obtained by the process according to the invention.

These halogen-substituted dibenzyl alcohols of the general formula (I) obtainable by the process according to the invention have a purity of at least about 98.5%. They comprise at most about 1.0%, preferably at most about 0.1%, particularly preferably at most about 0.01% of compounds substituted asymmetrically in the 1- and 4-positions, in particular halogen-substituted 1-(benzyl alcohol)-4-benzylamines, 1-benzaldehyde-4-benzyl alcohols and 1-(benzoic acid)-4-benzyl alcohols, and, in particular, they are completely free of these compounds. The proportion required to make up 100 is due to other impurities which enter the system via the starting materials in the initial steps leading to the halogen-substituted terephthalic acids and are carried over into the end product.

These particularly pure halogen-substituted dibenzyl alcohols are suitable for use as intermediates in the preparation of pharmaceutically and agrochemically active compounds.

Here, the person skilled in the art can refer to the extensive literature for example on the preparation of household insecticides, for example EP-A-0 963 976, EP-A-0 959 065, EP-A-0 302 612 and EP-A-0 926 129.

The invention is further described in the following illustrative examples in which all parts and percentages are by weight unless otherwise indicated.

EXAMPLES

Example 1

Acid Hydrolysis of 2,3,5,6-tetrafluoroterephthalic Acid 7320 g of 98% strength sulfuric acid were initially charged together with 30 g of sodium silicate and 30 g of silicone oil and heated at 100° C. 6 portions of in each case 254.2 g of tetrafluoroterephthalonitrile were added. The mixture was then heated to 170° C. and stirred at this temperature for 1 hour. At 170° C., 2440 g of water were metered in over 3 h. The mixture was then allowed to cool to 20° C. and the precipitated solid was filtered off. The residue was washed twice with in each case 500 g of water and dried. 1769.0 g of tetrafluoroterephthalic acid having a content of 96% (remainder ad 100% inorganic components of the silicates) (99.5% yield) were obtained.

Example 2

Borohydride Reduction with Dimethyl Sulfate of 2,3,5,6-tetrafluoroterephthalic Acid to give 2,3,5,6-tetrafluorodibenzyl Alcohol.

In a 16 liter reactor made of glass, 534.5 g of sodium borohydride and 3000 g of 1,2-dimethoxyethane were initially charged. The content of the reactor was stirred at 60° C. under an atmosphere of nitrogen for 3 h. At 60° C., 4200 g of a 33.3% by weight solution of 2,3,5,6-tetrafluoroterephthalic acid in 1,2-dimethoxyethane were then metered in over a period of 10 h (prior to the use, the solution was freed by filtration of in-organic components resulting from the hydrolysis). The reactor content was stirred at 60° C. until the evolution of gas had ceased. It was cooled to 50° C., and 2000 g of toluene were then added. A 21.5% by weight solution of 1480.9 g of dimethyl sulfate and 5400 g of toluene was then added at 50° C. over a period of 10 h. The reactor content was stirred at 50° C. until the evolution of gas had ceased. The reactor content was then heated at 75° C. for 1 h and subsequently at reflux. The solvent was exchanged by addition of toluene with simultaneous distillative removal of 1,2-dimethoxyethane.

The distillation ended when the reactor content was reduced by distillation to about 8 liters and virtually no more 1,2-dimethoxyethane distills over.

The mixture was cooled to 65° C., and 4500 g of water were added over a period of 2 h. The mixture was heated at 90° C. and stirred for 10 h. The mixture was then cooled to 60° C., 1500 g of ethyl acetate were added and the mixture was stirred for 0.5 h. The phases were separated. The aqueous phase was extracted twice with in each case 5000 g of ethyl acetate. The combined organic phases are concentrated to 12 liters where, if necessary, 3000 g of toluene may be exchanged by distillation for ethyl acetate. At 80° C., the mixture was washed with 500 g of saturated sodium carbonate solution and then cooled to 20° C. The precipitated solvent was isolated by filtration and, if required, washed with 1000 g of toluene to remove the adhering mother liquor. The product was dried. This gave 1123.5 g (90.5%) of a colourless solid having a purity of 98.7%.

Example 3

Borohydride Reduction with Sulfuric Acid of 2,3,5,6-tetrafluoroterephthalic Acid to give 2,3,5,6-tetrafluorodibenzyl Alcohol In a 16 liter reactor made of glass, 617.5 g of sodium borohydride and 1950 g of 1,2-dimethoxyethane were initially charged. At 60° C., 3900 g of a 31.5% by weight solution of 2,3,5,6-tetrafluoroterephthalic acid in 1,2-dimethoxyethane were then metered in over a period of 10 h. The reactor content was stirred at 60° C. until the evolution of gas had ended. The content was cooled to 50° C., and 2000 g of toluene were then added. 793 g of 98% strength sulfuric acid and 1549 g of toluene were then added simultaneously at 50° C. over a period of 10 h. The reactor content was stirred at 65° C. until the evolution of gas ceased. The solvent was ex-changed by addition of toluene with simultaneous distillative removal of 1,2-dimethoxyethane.

The distillation ended when the reactor content had been reduced by distillation to about 8 liters and virtually no more 1,2-dimethoxyethane distills over.

The mixture was cooled to 65° C., and 3640 g of 5% strength aqueous sodium hydroxide solution were added over a period of 2 h. The mixture was heated at 90° C. and stirred for 3 h. The mixture was then cooled to 60° C., 1500 g of ethyl acetate and 500 g of water were added and the mixture was stirred for 0.5 h. The phases were separated. The aqueous phase was extracted once with 4550 g of ethyl acetate. The combined organic phases were concentrated to 6 liters and then cooled to 20° C. The precipitated solid was isolated by filtration and, if required, washed with 650 g of toluene to remove the adhering mother liquor. The product was dried. 661.2 g (60.4%) of a colourless solid having a purity of 99.1% were obtained.

Comparative Example

Preparation of 2,3,5,6-tetrafluoroxylylidenediamine as a Solution in Sulfuric Acid.

1249.5 g of 2,3,5,6-tetrafluoroterephthalonitrile (6.24 mol) together with 750 ml of methanol, 5250 ml of water, 1050 g of concentrated sulfuric acid and 75 g of a 5% palladium/carbon catalyst were initially charged in a 10 l autoclave and hydrogenated at 30° C. and a hydrogen pressure of 30 bar until the pressure remained constant. The catalyst was filtered off. The methanol was then distilled off at 80–90° C. and 350 mbar. This gave 6690 g of a solution in sulfuric acid which, according to GC analysis (external standard), contained 1197.2 g (5.75 mol) of tetrafluoroxylylidenediamine (92% yield).

Preparation of 2,3,5,6-tetrafluorodibenzyl alcohol.

3200 g of the tetrafluoroxylylidenediamine hydrosulfate solution was prepared as above in Comparative Example 1.

(2.87 mol of compound) were adjusted to pH 4 using 868 g of 20% strength sodium hydroxide solution. The reaction mixture was heated at 80–90° C., and 981 g of a 40% strength sodium nitrite solution were added dropwise over a period of 4 h. Using 127 g of 30% strength sulfuric acid, the pH of the solution was simultaneously maintained between pH 3 and pH 5. After the evolution of gas had ceased, the reaction mixture was extracted twice with 750 ml of ethyl acetate and the organic phase was then concentrated under reduced pressure. 456 g (2.17 mol) of 2,3,5,6-tetrafluoroxylylidenediol having a purity of 74.5%, in a yield of 76% were obtained.

Although the present invention has been described in detail with reference to certain preferred versions thereof, other variations are possible. Therefore, the spirit and scope of the appended claims should not be limited to the description of the versions contained therein.

What is claimed is:

1. A process for preparing a halogen-substituted dibenzyl alcohol of the general formula (I):

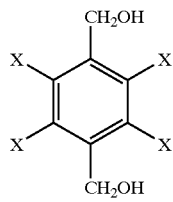

(I)

wherein the radicals X are identical or different and are hydrogen, fluorine, chlorine or bromine and at least one X is fluorine, chlorine or bromine, the process comprising reacting (1) a halogen-substituted terephthalic acid of the general formula (II)

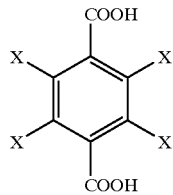

(II)

wherein the radicals X are as defined for the general formula (I) with (2) sodium borohydride and then with (3) an alkylating agent or sulfuric acid or an alkyl-sulfonic acid or an arylsulfonic acid, wherein the sulfuric acid or the alkyl-sulfonic acid or the arylsulfonic acid comprises at most 5% by volume of water and the sodium borohydride reacts in an organic solvent at a temperature ranging from about 0 to about 150° C.

2. The process according to claim 1, wherein the halogenated terephthalic acid of the general formula (II) is 2,3,5,6-tetrafluoro- or 2,3,5,6-tetrachloroterephthalic acid.

3. The process according to claim 1, wherein in the halogenated terephthalic acid of the general formula (II), two X are hydrogen and one X is chlorine or fluorine.

4. The process according to claim 1, wherein the halogenated terephthalic acid of the general formula (II) is obtained by acid hydrolysis of halogenated terephthalonitrile of the general formula (III)

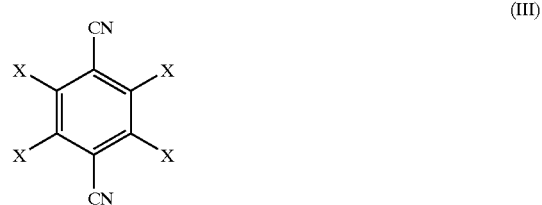

(III)

wherein the radicals X are as defined for the general formula (II).

5. The process according to claim 1, wherein reaction with sodium borohydride reacts at a temperature ranging from about 20 to about 80° C. or from about 40 to about 65° C.

6. The process according to claim 1, wherein the organic solvent is an aprotic polar organic solvent.

7. The process of claim 1, wherein the organic solvent is selected from the group consisting of diethyl ether, diisopropyl ether, diisobutyl ether, methyl t-butyl ether, 1,2-dimethoxyethane, diglycol dimethyl ether, tetrahydrofuran, 1,4-dioxane, and mixtures thereof.

8. The process according to claim 1, wherein from about 2.0 to about 2.5 mol of sodium borohydride is used per mole of the halogenated terephthalic acid of the general formula (II) and an alkylating agent is then added.

9. The process according to claim 1, wherein from about 2.0 to about 4.0 mol of sodium borohydride is used per mole of halogenated terephthalic acid of the general formula (II) and sulfuric acid or an alkylsulfonic acid or an arylsulfonic acid is then added.

10. The process according to claim 1, wherein the alkylating agent is an alkyl halide, dialkyl sulfate or a sulfonic ester of the general formula (III), (IV) or (V)

R—Hal (III)

RO—SO$_2$—OR$^2$ (IV)

R—SO$_2$—OR$^2$ (V)

wherein R and R$^2$ independently of one another are methyl, ethyl, propyl, isopropyl, n-butyl, isobutyl, tert-butyl, phenyl or tolyl and Hal is Cl, Br or I.

11. The process according to claim 1, wherein the alkyl-sulfonic acid is methylsulfonic acid, ethylsulfonic acid, propylsulfonic acid or butylsulfonic acid.

12. The process of claim 1, wherein the arylsulfonic acid is phenylsulfonic acid or tolylsulfonic acid.

13. The process according to claim 1, wherein reaction with the alkylating agent, the sulfuric acid or the alkylsulfonic acid or arylsulfonic acid is carried out at a temperature ranging of from about 0 to about 150° C.

* * * * *